US011653941B2

(12) United States Patent
Augustin et al.

(10) Patent No.: US 11,653,941 B2
(45) Date of Patent: May 23, 2023

(54) INFLATABLE BALLOON FOR MEDICAL USE

(71) Applicant: DIANOSIC, Malakoff (FR)

(72) Inventors: Marc Augustin, Paris (FR); Philippe Bastide, Issy-les-Moulineaux (FR)

(73) Assignee: DIANOSIC, Strasbourg (FR)

( * ) Notice: Subject to any disclaimer, the term of this patent is extended or adjusted under 35 U.S.C. 154(b) by 607 days.

(21) Appl. No.: 16/635,353

(22) PCT Filed: Jul. 19, 2018

(86) PCT No.: PCT/FR2018/051847
§ 371 (c)(1),
(2) Date: Jan. 30, 2020

(87) PCT Pub. No.: WO2019/025694
PCT Pub. Date: Feb. 7, 2019

(65) Prior Publication Data
US 2020/0367916 A1 Nov. 26, 2020

(30) Foreign Application Priority Data

Aug. 3, 2017 (FR) ...................................... 1757465

(51) Int. Cl.
*A61B 17/22* (2006.01)
*G16H 40/67* (2018.01)
(Continued)

(52) U.S. Cl.
CPC .............. *A61B 17/22* (2013.01); *A61B 5/145* (2013.01); *A61B 5/6819* (2013.01);
(Continued)

(58) Field of Classification Search
CPC ... A61B 5/0075; A61B 5/145; A61B 5/14532; A61B 5/14552; A61B 5/6819;
(Continued)

(56) References Cited

U.S. PATENT DOCUMENTS 7,892,162 B1 * 2/2011 Jeevanandam ..... A61M 60/843
600/18
8,894,614 B2 11/2014 Muni et al.
(Continued)

FOREIGN PATENT DOCUMENTS

CN 104055525 A 9/2014
JP 2002-011101 A 1/2002
(Continued)

OTHER PUBLICATIONS

International Search Report, dated Nov. 2, 2018, from corresponding PCT application No. PCT/FR2018/051847.
(Continued)

*Primary Examiner* — Jocelin C Tanner
(74) *Attorney, Agent, or Firm* — Nixon & Vanderhye

(57) ABSTRACT

This inflatable balloon includes a balloon body, an inflation opening for the introduction of a fluid into the balloon body so as to inflate it under pressure, and at least one device for measuring a biological quantity of cavity tissues and/or of biological fluids present in this cavity. The measuring device includes an external sensor attached on an external face of the wall of the balloon body and adapted to supply an electrical measurement signal sensitive to the measured biological quantity, and an internal module located inside the balloon body and including a processing device adapted to process the electrical measurement signal in order to provide at least one measurement of the biological quantity.

18 Claims, 2 Drawing Sheets

(51) Int. Cl.
*A61B 5/00* (2006.01)
*A61B 17/24* (2006.01)
*A61B 17/12* (2006.01)
*A61B 5/145* (2006.01)
*A61B 17/00* (2006.01)

(52) U.S. Cl.
CPC .............. *A61B 5/6853* (2013.01); *A61B 5/74* (2013.01); *A61B 17/12104* (2013.01); *A61B 17/12136* (2013.01); *A61B 17/24* (2013.01); *G16H 40/67* (2018.01); *A61B 2017/00022* (2013.01); *A61B 2017/12004* (2013.01); *A61B 2017/22062* (2013.01); *A61B 2560/0406* (2013.01); *A61B 2562/02* (2013.01); *A61B 2562/164* (2013.01); *A61B 2562/166* (2013.01); *A61B 2562/18* (2013.01)

(58) Field of Classification Search
CPC ... A61B 5/6853; A61B 5/74; A61B 17/12104; A61B 17/12136; A61B 17/22; A61B 17/24; A61B 2017/00022; A61B 2017/12004; A61B 2017/22062; A61B 2560/0406; A61B 2562/02; A61B 2562/164; A61B 2562/166; A61B 2562/18; G16H 40/67
See application file for complete search history.

(56) References Cited

U.S. PATENT DOCUMENTS

| | | |
|---|---|---|
| 10,687,838 B2 | 6/2020 | Augustin et al. |
| 2005/0245906 A1 | 11/2005 | Makower et al. |
| 2006/0000472 A1 | 1/2006 | Fenton |
| 2006/0004286 A1* | 1/2006 | Chang .................... A61B 90/16 606/198 |
| 2007/0010709 A1 | 1/2007 | Reinschke |
| 2007/0161851 A1 | 7/2007 | Takizawa et al. |
| 2010/0087782 A1 | 4/2010 | Ghaffari et al. |
| 2010/0094209 A1* | 4/2010 | Drasler ............. A61M 25/1002 604/95.04 |
| 2011/0010925 A1 | 1/2011 | Nix et al. |
| 2011/0105865 A1 | 5/2011 | Yu et al. |
| 2012/0245553 A1* | 9/2012 | Raven .................. A61N 1/0509 604/98.01 |
| 2013/0304052 A1* | 11/2013 | Rizq ...................... A61B 18/18 606/41 |
| 2015/0051449 A1 | 2/2015 | Qiu |
| 2015/0359996 A1* | 12/2015 | Arora ............. A61M 25/0017 600/300 |
| 2016/0166203 A1 | 6/2016 | Goldstein et al. |
| 2018/0360634 A1* | 12/2018 | Rosenberg ........... A61F 5/0026 |

FOREIGN PATENT DOCUMENTS

| | | |
|---|---|---|
| JP | 2005-028189 A | 2/2005 |
| JP | 2006-102361 A | 4/2006 |
| JP | 2007-082954 A | 4/2007 |
| JP | 2009-528085 A | 8/2009 |
| JP | 2009-291476 A | 12/2009 |
| JP | 2011-115614 A | 6/2011 |
| JP | 2012-505041 A | 3/2012 |
| JP | 2017-512604 A | 5/2017 |
| WO | 2010/042653 A1 | 4/2010 |
| WO | 2016/065082 A1 | 4/2016 |
| WO | 2016/067153 A1 | 5/2016 |
| WO | 2016/179563 A1 | 11/2016 |
| WO | 2017/064437 A1 | 4/2017 |

OTHER PUBLICATIONS

Office Action issued in Japanese Patent Application No. 2020-505456 dated Apr. 5, 2022.
Office Action issued in Chinese Patent Application No. 201880060180.9 dated Jul. 28, 2022.

* cited by examiner

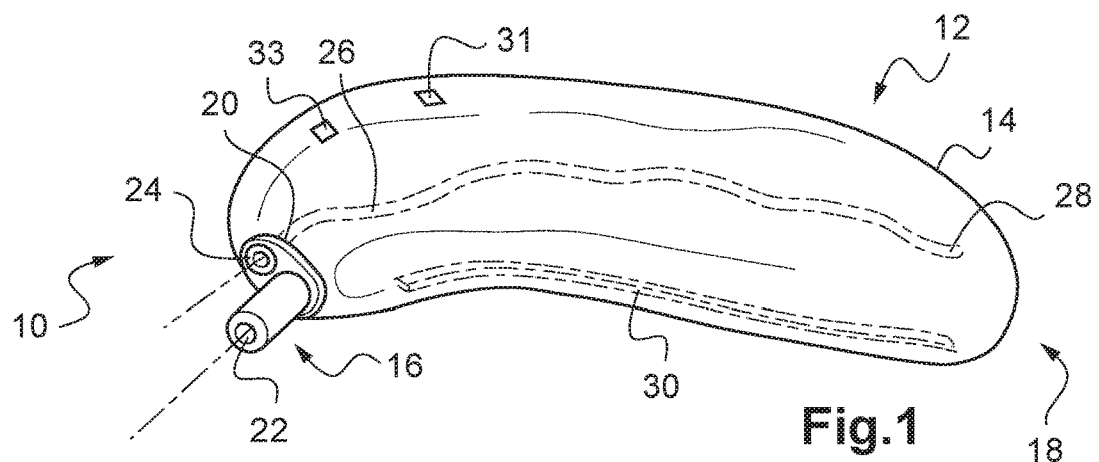
Fig.1
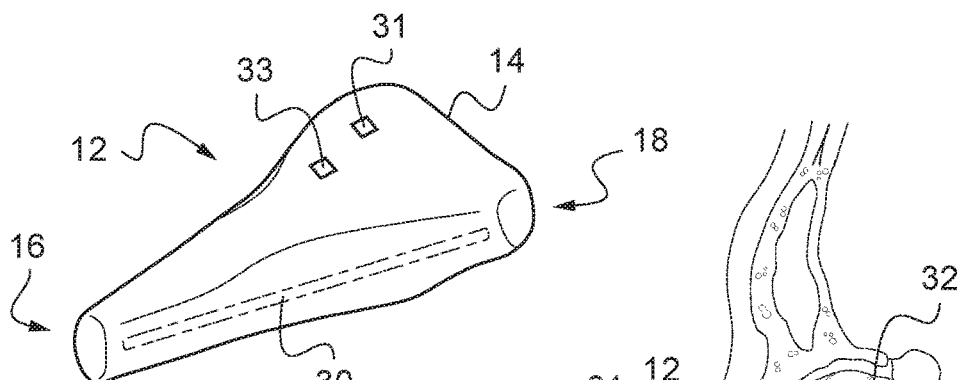
Fig.2
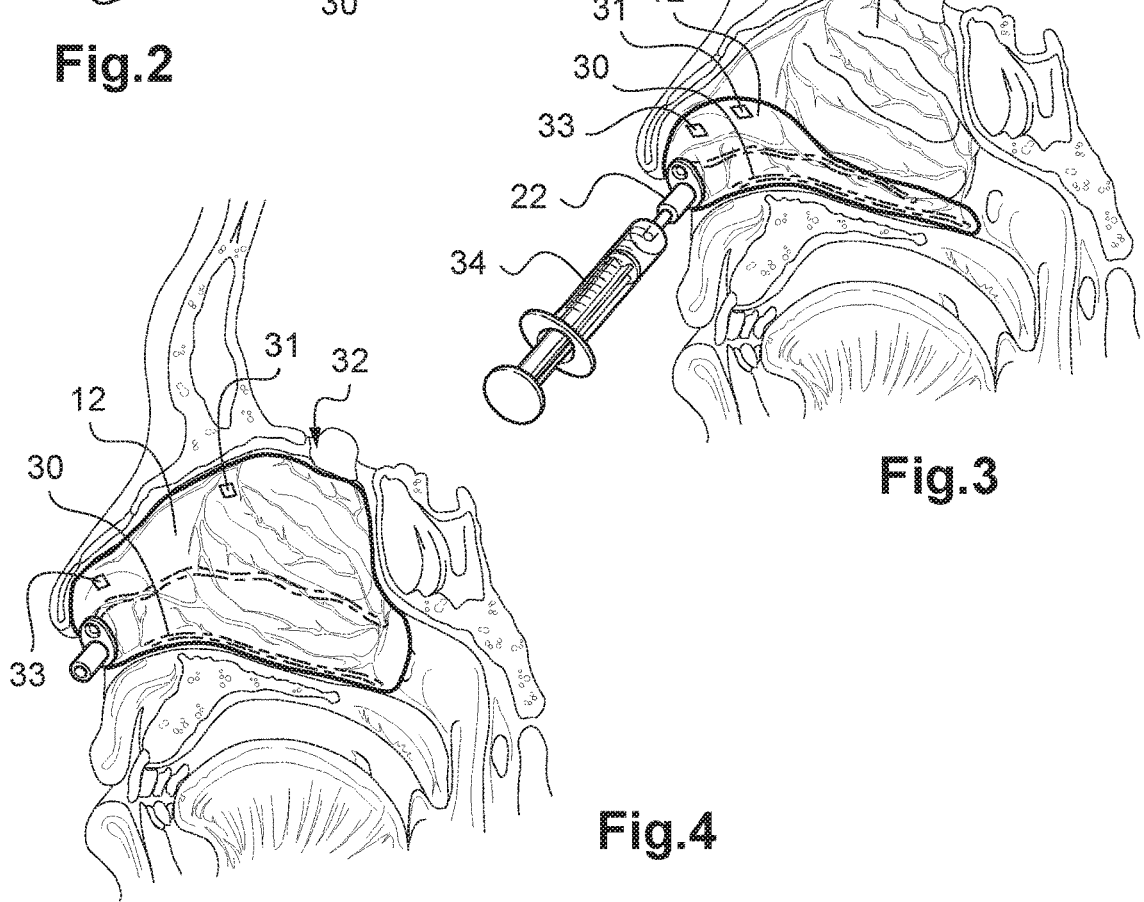
Fig.3
Fig.4

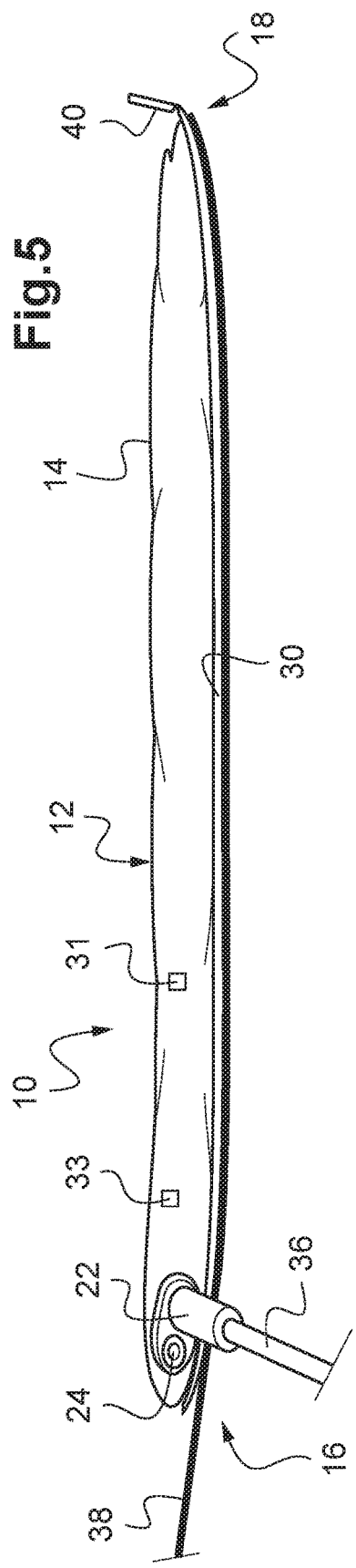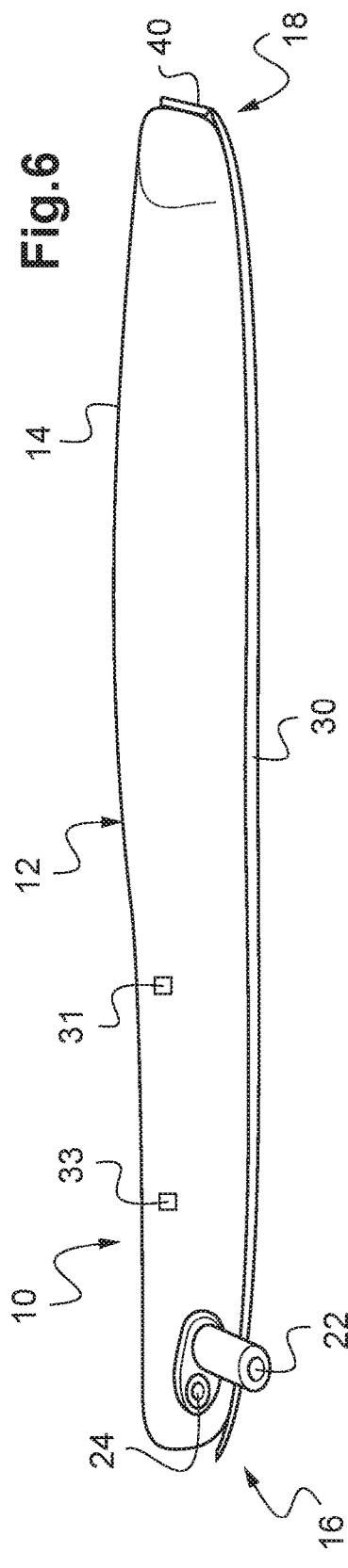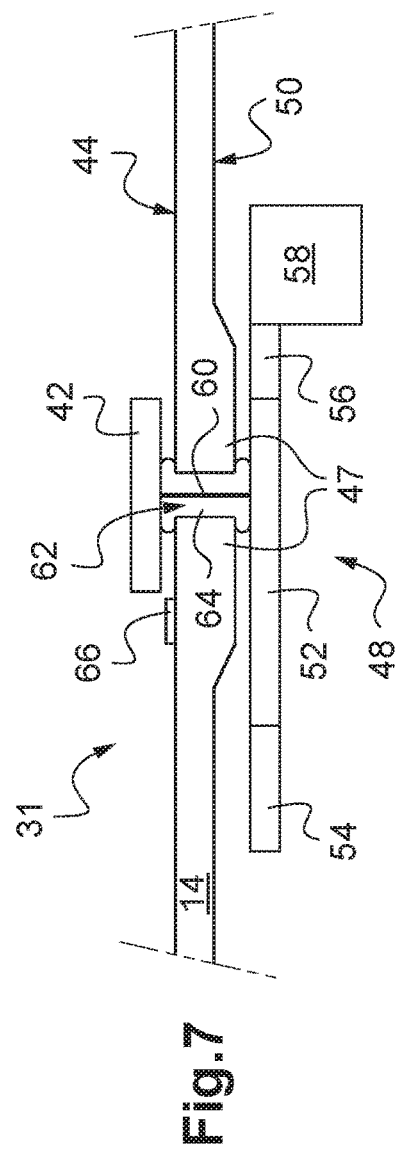

INFLATABLE BALLOON FOR MEDICAL USE

The present invention relates to an inflatable balloon for medical use, intended to be inserted deflated into a cavity of a human or animal body then inflated inside this cavity in order to press against the walls of this cavity.

In otorhinolaryngology for example, a balloon of this type is inserted into the nasal cavity of a patient, then inflated once correctly positioned using a fluid such as air, gelled water or physiological serum. A common application of this type of balloon is the treatment of hemorrhages by pressing against the internal walls of the nasal cavity.

More particularly, the invention applies to a balloon for medical use, intended to be inserted deflated into a cavity of a human or animal body then inflated inside this cavity in order to press against it, including:
- a balloon body the wall of which is made of flexible inflatable material,
- an inflation opening for introducing a fluid into the balloon body so as to inflate it under pressure, and
- at least one device for measuring a biological quantity of biological tissues of the cavity and/or of the biological fluids present in this cavity.

This type of balloon is for example described in the PCT international patent application published under number WO 2016/067153 A1. In this publication, the measuring device is intended to measure the oxygen "pulsed" saturation, also called SpO2.

In a general manner, it can be delicate to place a measuring device on the external face of a balloon body. Indeed, the measuring device must protrude the least possible so as not to impede the flow of fluids in the cavity and/or not to irritate the biological tissues of the cavity. However, it is necessary to provide a casing to protect the electronics of the measuring device from aggressions of the biological medium of the cavity, as described for example in the Chinese patent application published under number CN 104055525 A. The presence of this casing increases the size of the measuring device and increases the space requirement thereof, so that it is difficult to make a measuring device of low projection.

It may thus be desired to provide an inflatable balloon for medical use which allows dispensing with at least some of the above-mentioned problems and constraints.

Therefore, a balloon for medical use is proposed, intended to be inserted deflated into a cavity of a human or animal body then inflated inside this cavity in order to press against it, including:
- a balloon body the wall of which is made of flexible inflatable material,
- an inflation opening formed for introducing a fluid into the balloon body so as to inflate it under pressure, and
- at least one device for measuring a biological quantity of biological tissues of the cavity and/or of the biological fluids present in this cavity,
characterized in that the measuring device includes:
- an external sensor attached on an external face of the wall of the balloon body and designed to provide an electrical measurement signal sensitive to the measured biological quantity, and
- an internal module located inside the balloon body and including a processing device designed to process the electrical measurement signal in order to provide at least one measurement of the biological quantity.

Thus, only the external sensor protrudes from the external face of the balloon body, so that the measuring device has a reduced projection. Furthermore, it is no longer necessary to provide a protective casing for the internal module, since the latter is in a non-aggressive environment, generally air, gelled water or physiological serum.

Optionally, the external sensor transmits the electrical measurement signal to the internal module by means of one or more electrical wire(s) passing through one or more conduit(s) formed through the wall of the balloon body.

Also optionally, a sealing material obstructs the conduit(s).

Also optionally, the sealing material includes a glue attaching the sensor to the external face of the wall of the balloon body.

Also optionally, the internal module is attached on an internal face of the wall of the balloon body.

Also optionally, the sealing material includes a glue attaching the internal module to the internal face of the wall of the balloon body.

Also optionally, the internal module further includes a wireless communication device designed to communicate the measurement of the biological quantity to a device located outside the human or animal body whereinto the inflatable balloon is inserted.

Also optionally, the internal module further includes a memory for storing the biological quantity measurement.

Also optionally, the external sensor is printed on the external face of the wall of the balloon body.

Also optionally, the inflatable balloon for medical use is for use in otorhinolaryngology or in neurosurgery and the balloon body is pre-formed to conform to the internal shapes of a nasal cavity of a human or animal body when it is inflated.

The invention will be better understood using the following description, given only by way of example and made with reference to the appended drawings wherein:

FIG. 1 schematically shows the general structure of an inflatable balloon for medical use, according to an embodiment of the invention, FIG. 2 illustrates an exemplary shape for the balloon of FIG. 1, FIGS. 3 and 4 illustrate arrangements of the balloon of FIG. 1 in a nasal cavity, before and after inflation, FIGS. 5 and 6 schematically show the general structure of an inflatable balloon for medical use, according to another embodiment of the invention, before and after inflation, and FIG. 7 schematically shows a device for measuring a biological quantity, attached to a wall of the inflatable balloon.

The inflatable balloon 10 for medical use schematically shown in FIG. 1 includes a balloon body 12, the wall 14 of which is made of flexible inflatable material, for example of silicone or any other equivalent material having these properties. It is intended to be inserted deflated into a cavity of a human or animal body, for example the nasal fossa, then inflated inside this cavity in order to press against it. It is of a generally elongated shape, having a proximal inflation end 16 and a distal positioning end 18 at the back of the cavity. The exterior of the wall 14 is advantageously coated with a slippery product and not aggressive for the biological tissues of the cavity.

The proximal end 16 includes a rigid support 20 which has a first opening and an inflation end piece 22 leading to this first opening. This end piece 22 facilitates the introduction of a syringe to inflate the balloon body 12 under pressure using a fluid such as air, gelled water, physiological serum, or any other suitable fluid. It can be provided with a valve, or any system suitable for inflation, so as to allow an injection or an aspiration of fluid without any leakage when the syringe or the inflation device is removed.

Furthermore, the rigid support 20 optionally has a second opening 24 intended to introduce an endoscope into the balloon body 12. This second opening 24 is for example in the form of a valve or any system allowing to introduce an endoscope while preventing any escape of the fluid introduced into the balloon body 12.

In this case, it is advantageous or even necessary for the fluid to be as transparent or translucent as possible for a better observation of the environment by the endoscope inside the balloon 10.

Also in this case, the balloon 10 may further include an elongated sock 26 extending inside the balloon body 12 and having a closed distal end 28 not integral with the wall 14 of the balloon body 12. An elongated sock must be understood as an elongated cap, of a shape complementary to that of the endoscope, inside which opens the second opening 24. It allows introducing the endoscope without contact of the latter with the fluid present in the body balloon 12. It is advantageously formed of a flexible material which is optionally elastic, for example of silicone or any material of the same nature.

The wall 14 of the balloon body 12 locally has an elongated portion 30, called the sole, of a greater rigidity than the rest of the wall 14, this sole 30 extending from the proximal end 16 to the distal end 18. It forms the base of the balloon body 12, facilitating the introduction and maintenance of the balloon 10 into the desired cavity even when the balloon is deflated. Moreover, it performs a guide function during inflation of the balloon 10, by giving it a prestressed direction.

In practice, the sole 30 can be an add-on part added against the wall 14 of the balloon body 12, consisting of any material ensuring the desired rigidity function. This material can be selected in a non-limiting manner from polymers such as polyvinyl chloride, polysiloxane, polyurethane, polyethylene polycarbonate, methyl polymethacrylate, ethylene polyterephthalate, or from fluoropolymers such as polytetrafluoroethylene or polychlorotrifluoroethylene. Alternatively, it may be formed integrally with the rest of the wall 14 of the balloon body 12, but it then has a thickness substantially greater than the rest of this wall 14 to increase the rigidity thereof.

Moreover, the inflatable balloon 10 includes one or more device(s) 31 for measuring in situ at least one biological quantity of the biological tissues of the nasal cavity and/or of the biological fluids present in the latter. The biological quantity includes, for example, a hemoglobin level, a protein level, a glucose level, a lactic acid level or a lactate level.

The balloon 10 may further include one or more device(s) 33 for measuring the internal pressure of the balloon 10.

As illustrated in FIG. 2, the balloon 10 can be designed for use in otorhinolaryngology or in neurosurgery. In this case, the wall 14 of the balloon body 12 can be pre-formed to conform to the internal shapes of a nasal cavity of a human or animal body in inflated conformation.

FIG. 3 illustrates the positioning of the balloon 10 of FIGS. 1 and 2 in a nasal cavity 32, in deflated conformation. Thanks to the sole 30 of a greater rigidity than the rest of the wall 14 of the balloon body 12, the balloon 10 is easily introduced into the nasal cavity 32. Once positioned, a fluid is introduced through the end piece 22 into the balloon body 12 using a syringe 34. By proceeding this way, the pressure inside the balloon body is easily controlled.

This allows the balloon 10 to be inflated until the result illustrated in FIG. 4 is obtained, according to which the balloon body 12 occupies the entire interior space of the nasal cavity 32 by conforming to the shape of the walls thereof.

According to another embodiment illustrated in cross-section in FIG. 5, and using the same references as previously for the unchanged elements, the balloon 10 further includes a rigid removable introduction rod 36 extending outwardly in the extension of the end piece 22. This rigid rod 36 allows facilitating the installation of the balloon 10 in the cavity and can be broken or removed when this installation is correctly carried out. The balloon 10 can be inflated using the syringe 34 before or after this maneuver.

The balloon 10 of this other embodiment further includes a removable rigid placement wire 38, extending as reinforcement to the sole 30 along or within the latter. It is for example made of nickel-titanium alloy, this material having interesting properties of shape memory and elasticity.

Finally, the balloon 10 of this other embodiment includes a reinforcement 40 at the distal end 18 in the extension of the sole 30. This distal reinforcement 40 has, like the sole 30, a greater rigidity than the rest of the wall 14 of the balloon body 12 and is shaped, for example at an angle close to 90° relative to the sole 30, so as to prevent, in cooperation with the latter, any elongation of the balloon 10 during its inflation. It can concretely consist of an add-on part added at the distal end of the sole 30, consisting of any material ensuring the desired rigidity function. This material can be selected in a non-limiting manner from polymers such as polyvinyl chloride, polysiloxane, polyurethane, polyethylene polycarbonate, methyl polymethacrylate, ethylene polyterephthalate, or from fluoropolymers such as polytetrafluoroethylene or polychlorotrifluoroethylene.

The balloon 10 of this other embodiment is shown in deflated conformation in FIG. 5 and in inflated conformation, with removal of the rigid rod 36 and of the removable rigid wire 38, in FIG. 6.

With reference to FIG. 7, the measuring device 31 first includes an external sensor 42 attached on an external face 44 of the wall 14 of the balloon body 12 in order to come into contact with biological tissues of the nasal cavity and/or biological fluids present in the latter when the balloon 12 is inflated in the cavity. The external sensor 42 is adapted to provide, spontaneously or in response to an electrical bias, an electrical measurement signal sensitive to the measured biological quantity. The electrical measurement signal is for example an analog signal, such as an electric current or an electric voltage.

For example, in the case where the measured biological quantity is the glucose level, the external sensor 42 can have two electrodes. Thus, when an electrical bias in the form of an electric voltage is applied to the external sensor 42, the latter provides an electrical signal in the form of an electric current that depends on the glucose level in the biological tissues and/or in the biological fluids present between the electrodes.

In another example where the measuring device 31 operates according to the diffuse reflectance spectroscopy principle, the external sensor 42 may include an emitter of electromagnetic radiation (for example, light) intended to interact with a tissue mass and at least one receptor of electromagnetic radiation that has interacted with the tissue mass. The receptor may comprise one or more photodiode(s), without being limited thereto. An example of a diffuse reflectance spectroscopy device is for example described in the American patent application published under number US 2011/0105865 A1.

The external sensor 42 preferably has a thickness of less than 0.5 mm, more preferably less than 0.3 mm, in order to be as flush as possible with the wall 14 of the balloon body 12. For example, the external sensor 42 can be a sensor printed on the external face 44 of the wall 14 of the balloon body 12. In this case, it generally has a thickness comprised between 0.1 and 0.3 mm. This type of sensor further has the advantage of well resisting the deformation of the balloon body 12.

Preferably, the wall 14 of the balloon body 12 locally has, at the external sensor 42, a portion 47, called reinforcement, of a greater rigidity than the rest of the wall 14. In practice, as for the sole 30, the reinforcement 47 may be an add-on part added against the wall 14 of the balloon body 12, consisting of any material ensuring the desired rigidity function. Alternatively, and as shown in FIG. 7, the reinforcement 47 can be made integrally with the rest of the wall 14 of the balloon body 12, but it then has a thickness substantially greater than the rest of this wall 14 to increase the rigidity thereof. The reinforcement 47 allows locally avoiding excessive deformation of the balloon body 12 and therefore a deterioration of the external sensor 42 during inflation of the balloon 10.

The measuring device 31 further includes an internal module 48 located in the balloon body 12 in order to be protected from the biological fluids present in the nasal cavity. The internal module 48 is for example attached on an internal face 50 of the wall 14 of the balloon body 12.

The internal module 48 includes a processing device 52 intended to receive and process the electrical measurement signal in order to provide successive measurements of the biological quantity, preferably in digital form. The processing device 52 includes for example a printed circuit board. When the external sensor 42 is adapted to provide the electrical measurement signal in response to an electrical bias, the processing device 52 can be adapted to provide this bias.

The internal module 48 further includes a wireless communication device 54 adapted to communicate the measurements to an external device, preferably a computing device, located outside the human or animal body whereinto the balloon 10 is inserted. The computing device is for example a smartphone, a tablet or else a desktop computer.

Instead of or in addition to the wireless communication device 54, the internal module 48 can further include a memory 56 for storing the measurements, for example in order to read them once the balloon 10 extracted from the cavity.

The electronic module 48 can further include an electrical energy source 58, such as a chemical battery, to power supply its elements and particularly the processing device 52, the wireless communication device 54 and/or the memory 56.

The external sensor 42 transmits the electrical measurement signal to the internal module 48 by means of one or more electrical wire(s) 60 passing through one or more conduit(s) 62 formed through the wall 14 of the balloon body 12.

The sealing between the inside and the outside of the balloon 12 is ensured by means of a sealing material 64, such as a cross-linked gel, obstructing the conduit(s) 62. The sealing material 64 includes for example a glue allowing, in addition to its sealing function, the attachment of the sensor 42 to the external face 44 of the wall and/or the attachment of the internal module 48 to the internal face 50 of the wall 14.

Moreover, one or more radio-opaque marker(s) 66 can be provided on the wall 14 of the balloon body 12, for example on its external face 44. A radio-opaque marker 66 is for example provided in the proximity of each external sensor 42, for example within one millimeter. Thus, it is possible to view and control the position of the balloon body 12 and/or of the external sensor(s) 42 in order to ensure that they are well placed to correctly perform their function. When the external sensors 42 are directly visible by imaging (MRI, scanner, radioscopy, ultrasound, etc.), it is possible to dispense with the radio-paque markers 66.

The presence of the measuring device(s) 31 on the balloon body 12 thus allows remotely monitoring various biological parameters, the knowledge of which is useful in otorhinolaryngology, neurosurgery or any other medical specialty.

A dedicated software can be programmed to detect a deviation of the measurements relative to a normal interval within which they should be. In case of deviation detected, an automatic alert can be sent (for example by email or by short telephone message (SMS)) to the healthcare professional so that he warns, for example, the patient in whom the implant 10 is placed. Alternatively or in addition, the automatic alert can be sent directly to the patient, or else to a call processing center which will be responsible for calling the healthcare professional and/or the patient. Once the measurements have been obtained, they can be used by the healthcare professional in order to react to a potentially unforeseen event once the patient has left the hospital, or to perform or refine their diagnosis, thus allowing to personalize the treatment of the patient. Moreover, the measurements obtained can be used to build up or else supply registers or any other type of database.

It is clear that an inflatable balloon for medical use such as that described above allows obtaining measurements of biological quantities, without their presence disturbing the flow of biological fluids or damaging the biological tissues.

Given its simple structure, it is furthermore easy to design and manufacture, so that it can be used once and then discarded.

It is particularly adapted for medical operations of otorhinolaryngological, head and neck surgeries or else in neurosurgery. It can also be used in other surgical operations, in particular in orthopedics or digestive surgery. Without even talking about surgery, it can also be used as a simple compression device to treat all kinds of epistaxis or nasal fossae bleeding, such bleeding occurring for example commonly in consultation.

Moreover, it will be noted that the invention is not limited to the embodiments described above.

Particularly, the shapes of the sole 30 and of the distal reinforcement 40 can be adapted to all the desired applications. They are therefore potentially very diverse.

More generally it will be apparent to the person skilled in the art that various modifications can be made to the embodiments described above, in light of the teaching which has just been disclosed to them. In the claims which follow, the terms used should not be interpreted as limiting the claims to the embodiments described in the present description, but should be interpreted to include all the equivalents that the claims aim at covering due to their formulation and whose prediction is within the reach of the person skilled in the art by applying their general knowledge to the implementation of the teaching which has just been disclosed to them.

The invention claimed is:

1. An inflatable balloon (10) for medical use, intended to be inserted deflated into a cavity of a human or animal body then inflated inside this cavity in order to press against it, the inflatable balloon (10) comprising:
  a balloon body (12), a wall (14) of which is made of flexible inflatable material,
  an inflation opening (22) for the introduction of a fluid into the balloon body (12) so as to inflate the balloon body (12) under pressure, and
  at least one measuring device (31) for measuring a biological quantity of biological tissues of the cavity and/or of the biological fluids present in this cavity,
  wherein the at least one measuring device (31) includes:
  an external sensor (42) attached on an external face (44) of the wall (14) of the balloon body (12) and designed to supply an electrical measurement signal sensitive to the measured biological quantity, and
  an internal module (48) located inside the balloon body (12) and including a processing device (52) designed to process the electrical measurement signal in order to provide at least one measurement of the biological quantity,
  wherein the external sensor (42) transmits the electrical measurement signal to the internal module (48) by one or more electrical wire(s) (60) passing through conduit(s) (62) formed through the wall (14) of the balloon body (12), and
  wherein a sealing material (64) obstructs the conduit (s) (62).

2. The inflatable balloon (10) for medical use according to claim 1, wherein the sealing material (64) includes a glue.

3. The inflatable balloon (10) for medical use according to claim 1, wherein the internal module (48) is attached on an internal face (50) of the wall (14) of the balloon body (12).

4. The inflatable balloon (10) for medical use according to claim 3, wherein a sealing material (64) obstructs the conduit(s) (62) and includes a glue attaching the internal module (48) to the internal face (50) of the wall (14) of the balloon body (12).

5. The inflatable balloon (10) for medical use according to claim 1, wherein the internal module (48) further includes a wireless communication device (54) designed to communicate the at least one measurement of the biological quantity to a device located outside the human or animal body whereinto the inflatable balloon (10) is inserted.

6. The inflatable balloon (10) for medical use according to claim 1, wherein the internal module (48) further includes a memory (56) for storing the at least one biological quantity measurement.

7. The inflatable balloon (10) for medical use according to claim 1, wherein the external sensor (42) is a sensor printed on the external face (44) of the wall (14) of the balloon body (12).

8. The inflatable balloon (10) for medical use according to claim 1, wherein the external sensor (42) is attached on the external face (44) of the wall (14) of the balloon body (12) by a glue, the glue also obstructing the conduit(s) (62).

9. An inflatable balloon (10) for a use in otorhinolaryngology or neurosurgery, intended to be inserted deflated into a cavity of a human or animal body then inflated inside this cavity in order to press against it, the inflatable balloon (10) comprising:
  a balloon body (12), a wall (14) of which is made of flexible inflatable material,
  an inflation opening (22) for the introduction of a fluid into the balloon body (12) so as to inflate the balloon body (12) under pressure, and
  at least one measuring device (31) for measuring a biological quantity of biological tissues of the cavity and/or of the biological fluids present in this cavity,
  wherein the at least one measuring device (31) includes:
  an external sensor (42) attached on an external face (44) of the wall (14) of the balloon body (12) and designed to supply an electrical measurement signal sensitive to the measured biological quantity, and
  an internal module (48) located inside the balloon body (12) and including a processing device (52) designed to process the electrical measurement signal in order to provide at least one measurement of the biological quantity,
  wherein the balloon body (12) is pre-formed to conform to internal shapes of a nasal cavity (32) of a human or animal body when the inflatable balloon is inflated.

10. The inflatable balloon (10) for medical use according to claim 9, wherein the internal module (48) further includes a memory (56) for storing the at least one biological quantity measurement.

11. The inflatable balloon (10) for medical use according to claim 9, wherein the external sensor (42) is a sensor printed on the external face (44) of the wall (14) of the balloon body (12).

12. The inflatable balloon (10) for medical use according to claim 9, wherein the internal module (48) further includes a wireless communication device (54) designed to communicate the at least one measurement of the biological quantity to a device located outside the human or animal body whereinto the inflatable balloon (10) is inserted.

13. The inflatable balloon (10) for medical use according to claim 9, wherein the external sensor (42) is attached on the external face (44) of the wall (14) of the balloon body (12) by a glue, the glue also obstructing conduit(s) (62) formed through the wall (14) of the balloon body (12).

14. An inflatable balloon (10) for medical use, intended to be inserted deflated into a cavity of a human or animal body then inflated inside this cavity in order to press against it, the inflatable balloon (10) comprising:
  a balloon body (12), a wall (14) of which is made of flexible inflatable material,
  an inflation opening (22) for the introduction of a fluid into the balloon body (12) so as to inflate the balloon body (12) under pressure, and
  at least one measuring device (31) for measuring a biological quantity of biological tissues of the cavity and/or of the biological fluids present in this cavity,
  wherein the at least one measuring device (31) includes:
  an external sensor (42) attached on an external face (44) of the wall (14) of the balloon body (12) and designed to supply an electrical measurement signal sensitive to the measured biological quantity, and
  an internal module (48) located inside the balloon body (12) and including a processing device (52) designed to process the electrical measurement signal in order to provide at least one measurement of the biological quantity,
  wherein the internal module (48) is attached on an internal face (50) of the wall (14) of the balloon body (12).

15. The inflatable balloon (10) for medical use according to claim 14, wherein the internal module (48) further includes a wireless communication device (54) designed to communicate the at least one measurement of the biological quantity to a device located outside the human or animal body whereinto the inflatable balloon (10) is inserted.

16. The inflatable balloon (10) for medical use according to claim 14, wherein the external sensor (42) is attached on the external face (44) of the wall (14) of the balloon body

(12) by a glue, the glue also obstructing conduit(s) (62) formed through the wall (14) of the balloon body (12).

17. The inflatable balloon (10) for medical use according to claim 14, wherein the external sensor (42) is a sensor printed on the external face (44) of the wall (14) of the balloon body (12).

18. The inflatable balloon (10) for medical use according to claim 14, wherein the internal module (48) further includes a memory (56) for storing the at least one biological quantity measurement.

* * * * *